United States Patent [19]

Bernstein et al.

[11] Patent Number: 4,496,839
[45] Date of Patent: Jan. 29, 1985

[54] SYSTEM AND METHOD FOR REMOTE DETECTION AND IDENTIFICATION OF CHEMICAL SPECIES BY LASER INITIATED NONRESONANT INFRARED SPECTROSCOPY

[75] Inventors: Lawrence S. Bernstein, Bedford; Fritz Bien, Billerica, both of Mass.; John A. Jamieson, Chevy Chase, Md.

[73] Assignee: Spectral Sciences Incorporated, Burlington, Mass.

[21] Appl. No.: 439,071

[22] Filed: Nov. 3, 1982

[51] Int. Cl.³ .............................................. G01J 3/00
[52] U.S. Cl. .................................... 250/341; 250/253
[58] Field of Search .................. 250/341, 340, 458.1, 250/459.1, 253

[56] References Cited

U.S. PATENT DOCUMENTS

| | | | |
|---|---|---|---|
| 3,723,007 | 3/1973 | Leonard | 356/301 |
| 3,783,284 | 1/1974 | McCormack | 250/339 |
| 3,832,558 | 8/1974 | Fern et al. | 250/461.1 |
| 4,044,257 | 8/1977 | Kreuzer | 250/344 |
| 4,071,298 | 1/1978 | Falconer | 356/73 |
| 4,151,415 | 4/1979 | Lipke | 250/333 |
| 4,178,102 | 12/1979 | Riccardi et al. | 356/307 |
| 4,188,120 | 2/1980 | McDonald et al. | 356/318 |
| 4,195,930 | 4/1980 | Delhaye et al. | 356/301 |
| 4,236,071 | 11/1980 | Chimenti | 250/253 |
| 4,259,574 | 3/1981 | Carr et al. | 250/302 |
| 4,313,057 | 1/1982 | Gelbwachs | 250/458.1 |

OTHER PUBLICATIONS

K. B. Eisenthal and K. E. Rieckhoff, "Laser Induced Luminescence", *IBM Technical Disclosure Bulletin*, vol. 8, No. 7, (Dec. 1965), p. 983.

J. W. Robinson and J. L. Guagliardo, "Non-Selective Remote Sensing of Organic Pollutants by Laser Induced IR Flourescence", *Spectroscopy Letters*, vol. 7, No. 2, (1979), pp. 121-130.

*Primary Examiner*—Janice A. Howell
*Assistant Examiner*—Constantine Hannaher
*Attorney, Agent, or Firm*—Joseph S. Iandiorio

[57] ABSTRACT

Disclosed is a system and method for remote detection and identification of unknown chemical species in gaseous, aerosol, and liquid states. A pulsed infrared laser is directed at an unknown chemical mass which absorbs energy at the laser wavelength. Due to molecular energy transfer processes, the absorbed laser energy can be re-emitted in one or more wavelength regions nonresonant with the laser wavelength. The re-emitted energy is detected for a period of time which is comparable to or less than the characteristic time for the absorbed radiative energy to be dissipated as heat. The nonresonant infrared emission spectrum of the unknown chemical species is detected with several infrared detectors. The identity of the unknown species, as well as its range and concentration, may be established by comparison of its spectrum to that for known species.

17 Claims, 7 Drawing Figures

SYSTEM AND METHOD FOR REMOTE DETECTION AND IDENTIFICATION OF CHEMICAL SPECIES BY LASER INITIATED NONRESONANT INFRARED SPECTROSCOPY

FIELD OF INVENTION

This invention relates to a system and method for remote detection and identification of chemical species by laser initiated nonresonant infrared spectroscopy (LINIS), and more particularly to such a method and system employing infrared emission to detect unknown chemical species in gas, liquid or aerosol form.

BACKGROUND OF INVENTION

It is often necessary to detect the presence and identity of a pollutant, contaminant or toxic species remotely, quickly and accurately, such as in atmospheric or effluent monitoring and control. Fast, positive detection is also of critical importance in defense against biological and chemical attack. Fast identification not only provides the time to don protective clothing, but also to select the proper antidote. Positive identification is important because the wrong antidote can be as lethal as the chemical species. Also, protective clothing can significantly degrade the effectiveness of combat personnel so false alarms should be minimized.

Present detection techniques suffer from a number of shortcomings. Some operate at wavelengths where the chemical signatures are not easily distinguished; some sense reflected radiation of the same wavelength as the laser and are subject to interference from natural atmospheric or aerosol scattering at the laser wavelength. Others cannot operate remotely or can sense only gases or only liquids or only aerosols, which makes them less than optimum for portable detection on site or on the battlefield.

SUMMARY OF INVENTION

It is therefore an object of this invention to provide an improved technique for quick, positive detection of unknown chemical species.

It is a further object of this invention to provide such a technique which operates remotely to detect chemical species in gas, liquid or aerosol form.

It is a further object of this invention to provide such a technique which uses molecular nonresonant infrared detection.

It is a further object of this invention to provide such a technique which reduces interference by distinguishing the excitation wavelength from the emission wavelengths.

This invention results from the realization that a truly fast and accurate identification of an unknown chemical species can be made by striking the unknown species with radiation of a first wavelength to induce molecular excitation, and then sensing radiation at one or more other wavelengths during the period of enhanced emission following the excitation, to obtain a characteristic for comparison with characteristics of known species.

This invention features a system for remote detection and identification of chemical species by laser initiated nonresonant infrared spectroscopy including a laser source for providing radiation of a first wavelength and means for directing radiation at the first wavelength from the laser source to a remote mass of an unknown chemical species, which absorbs the radiation of the first wavelength and emits nonresonant radiation in one or more wavelength regions. There are means for receiving radiation from the mass of unknown chemical species and means, responsive to the means for receiving, for detecting the intensity of the received radiation. There are means for sampling the intensity of the received radiation after molecular excitation during the period of enhanced emission before relaxation to obtain a nonresonant emission spectrum characteristic of the unknown chemical species. There are means for comparing the characteristic of the unknown chemical species with the characteristics of known chemical species for determining the identity of the unknown chemical species.

In a preferred embodiment the duration of enhanced emission is $10^{-6}$ to $10^{-4}$ seconds after laser radiation absorption. The means for sampling may have sample intervals of 1-10 microseconds. The laser source may include an infrared laser which provides radiation in the 8-12 $\mu$m spectral region. Specifically, the laser source may be a $CO_2$ laser and provide radiation at 9.4 $\mu$m with emissions in the 8-14 $\mu$m range, and the laser is a pulsed laser.

The invention also features a method of remote detection and identification of chemical species by laser initiated nonresonant infrared spectroscopy in which radiation of a first wavelength is provided and directed to a remote mass of an unknown chemical species which absorbs the radiation in the first wavelength and emits nonresonant radiation in one or more wavelength regions. The radiation is received from the mass of unknown chemical species, and then the intensity of the received radiation is detected. The intensity of the received radiation is sampled after the molecular excitation during the period of enhanced emission before relaxation to obtain a nonresonant emission spectrum characteristic of the unknown chemical species. The characteristic of the unknown chemical species is then compared with the characteristics of known chemical species in order to determine the identity of the unknown chemical species.

DISCLOSURE OF PREFERRED EMBODIMENT

Other objects, features and advantages will occur from the following description of a preferred embodiment and the accompanying drawings, in which.

Figure 1:
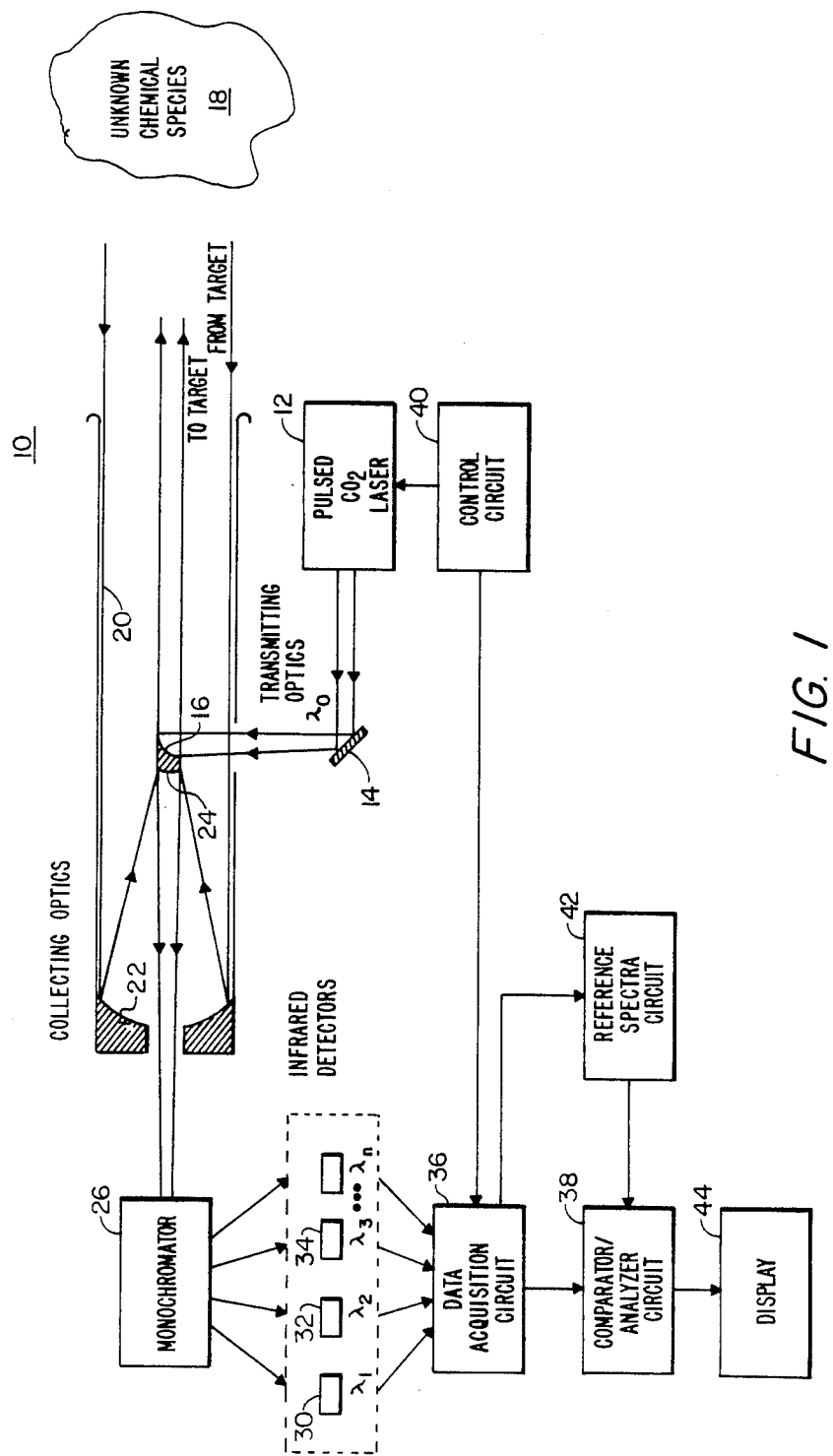
FIG. 1 is a schematic diagram of a system for remote detection and identification of chemical species by laser initiated nonresonant infrared spectroscopy according to this invention.

There is shown in FIG. 1 a system 10 for remote detection and identification of chemical species by laser initiated nonresonant infrared spectroscopy (LINIS) according to this invention including a $CO_2$ infrared laser 12, whose output at wavelength $\lambda_0 = 9.4$ m, is directed to steering expansion mirror 14 and then to steering collimating mirror 16 in the transmitting optics, from which it is directed to the unknown chemical species 18. The returning radiation 20 includes $\lambda_0$ plus emission radiation $\lambda_1$, $\lambda_2$, in the 8–14 μm range. The returning radiation 20, including the laser wavelength $\lambda_0$ and other wavelengths $\lambda_1$ and $\lambda_2$ emitted by the excited molecules of the chemical species, strikes primary collector mirror 22 and secondary collector mirror 24 in the collecting optics. From the collecting optics the returning radiation 20 is separated by monochromator 26 into the wavelengths $\lambda_0, \lambda_1, \lambda_2, \ldots$ and $\lambda_n$, which are sensed by detectors 30, 32 and 34, . . . . The outputs of detectors 30, 32 and 34 are delivered to data acquisition circuit 36, which provides to comparator/analyzer 38 the spectral characteristic from the outputs of detectors 30, 32 and 34. Comparator 38 compares the intensity of the spectral characteristic provided by detectors 30, 32 and 34 with that of known species from reference spectra circuit 42 to determine the identity of the unknown chemical species 18. The output of comparator/analyzer circuit 38 may be provided on a CRT, chart recorder, or other display 44. The reference characteristics stored in circuit 42 may be introduced from an external source or may be acquired empirically by operating the system with a number of known species as the target. Data acquisition circuit 36 may include more sophisticated identification circuits and may include additional processing circuits to determine range and concentration and to deal with clouds of multiple unknown chemical species. Control circuit 40 controls the firing of laser 12, and the sampling by data acquisition circuit 36 of the output of detectors 30, 32 and 34.

Figure 2:
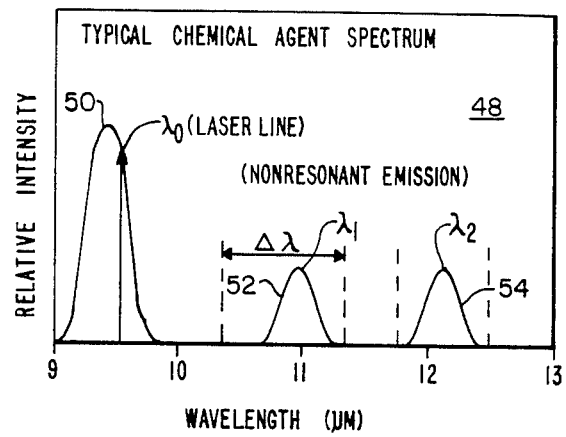
FIG. 2 is an illustration of a typical chemical species spectrum obtained from the system of FIG. 1.

A typical chemical species characteristic or spectrum 48, FIG. 2, includes a first peak 50, including laser line $\lambda_0$, and additional peaks 52 and 54, representing nonresonant emissions of the species at $\lambda_1$ and $\lambda_2$.

Figure 3:
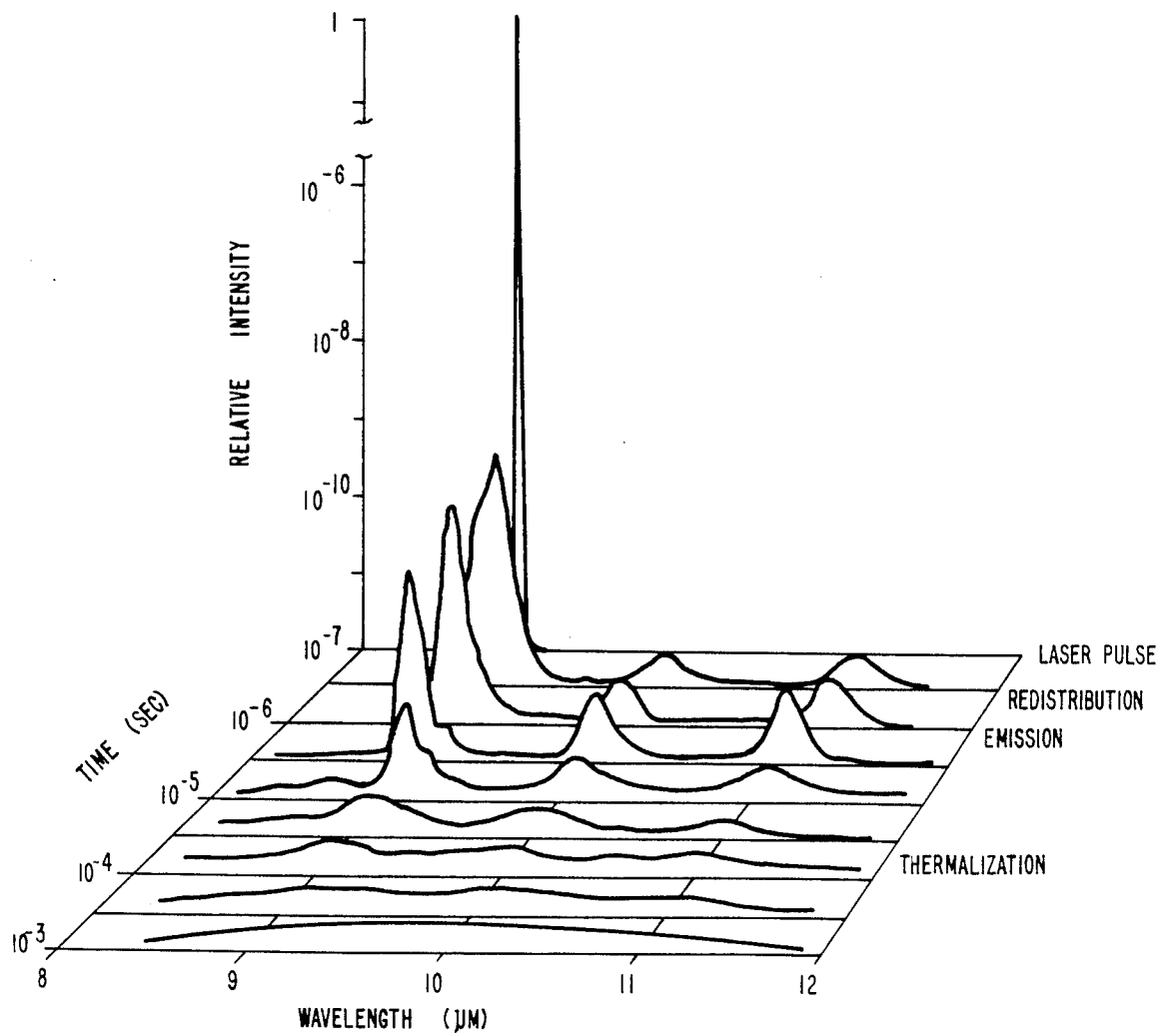
FIG. 3 is a three-dimensional plot of time versus intensity versus wavelength illustrating the basic molecular processes which occur following initial laser excitation.

The basic molecular physics of the detection technique of this invention are illustrated with a three-dimensional projection in FIG. 3. A pulsed laser is used to excite a vibrational-rotational state in the molecules of the chemical species 18. The population of initially excited states at the resonant laser wavelength $\lambda_0$ quickly relaxes both vibrationally and rotationally to a broad distribution which can re-emit nonresonantly wherever the molecule has an allowed absorption band, e.g., $\lambda_1$, $\lambda_2$. Rotational redistribution typically occurs on the near-gas kinetic time scale, on the order of $10^{-9}$ seconds at one atmosphere pressure. Vibrational redistribution, which can proceed intramolecularly (collisionally unassisted) and intermolecularly (collisionally assisted), typically occurs over a broader time range from a few hundred vibrational periods to near-gas kinetic, $10^{-12}$ to $10^{-9}$ seconds. Because of the large number of vibrational modes in a big molecule, within $10^{-9}$ seconds after laser photon absorption the excited molecule can be characterized by a vibrational temperature which is elevated significantly above the bulk gas temperature. Then, for a time scale on the order of vibrational quenching, typically 1–10 microseconds at one atmosphere, the excited molecules will produce an emission spectrum with intensities corresponding to the elevated temperature, although retaining a narrow rotational width corresponding to the bulk gas temperature. Improved detection efficency is obtained by using a laser pulse and a detector response time which are short compared with the vibrational quenching time. The same technique can be used to detect liquid phase chemicals in aerosol form (droplets) or as a film. The laser energy is selectively absorbed by the liquid, which causes the liquid to become superheated (elevated in temperature above the ambient temperature). The duration of the state of superheating is controlled by the process of thermal conduction, both into the air and into the cooler interior of the liquid. This process is comparable in duration to that for quenching of vibrational excitation in gas phase molecules, typically 1–10 microseconds. While the liquid is superheated it produces an emission spectrum with intensities corresponding to the elevated temperature.

Figure 4:
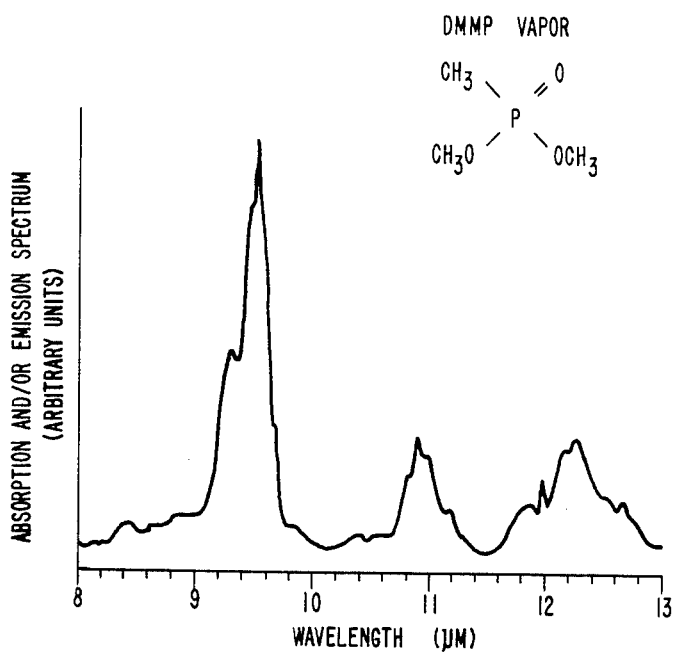
FIGS. 4 and 5 show typical spectra for DMMP vapor and VX liquid.
Figure 5:
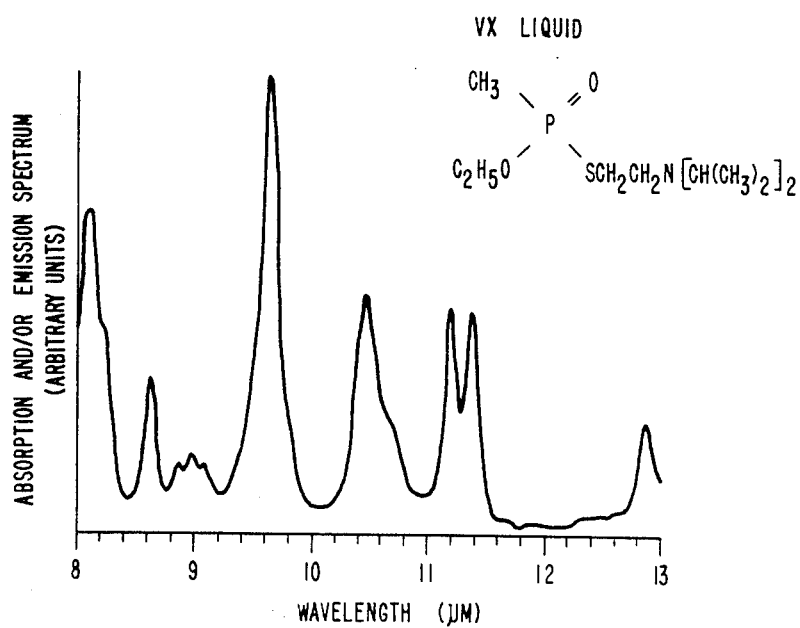

Detection of both gas and liquid phase chemical species is performed on the nonresonant enhanced (over the background) emission in the $\lambda_1$ and $\lambda_2$ bands. Identification of a specific chemical species, for example, is possible because the locations of $\lambda_1$ and $\lambda_2$ are generally different for each chemical species. The specific spectrum for DMMP vapor and VX liquid are shown in FIGS. 4 and 5.

Figure 6:
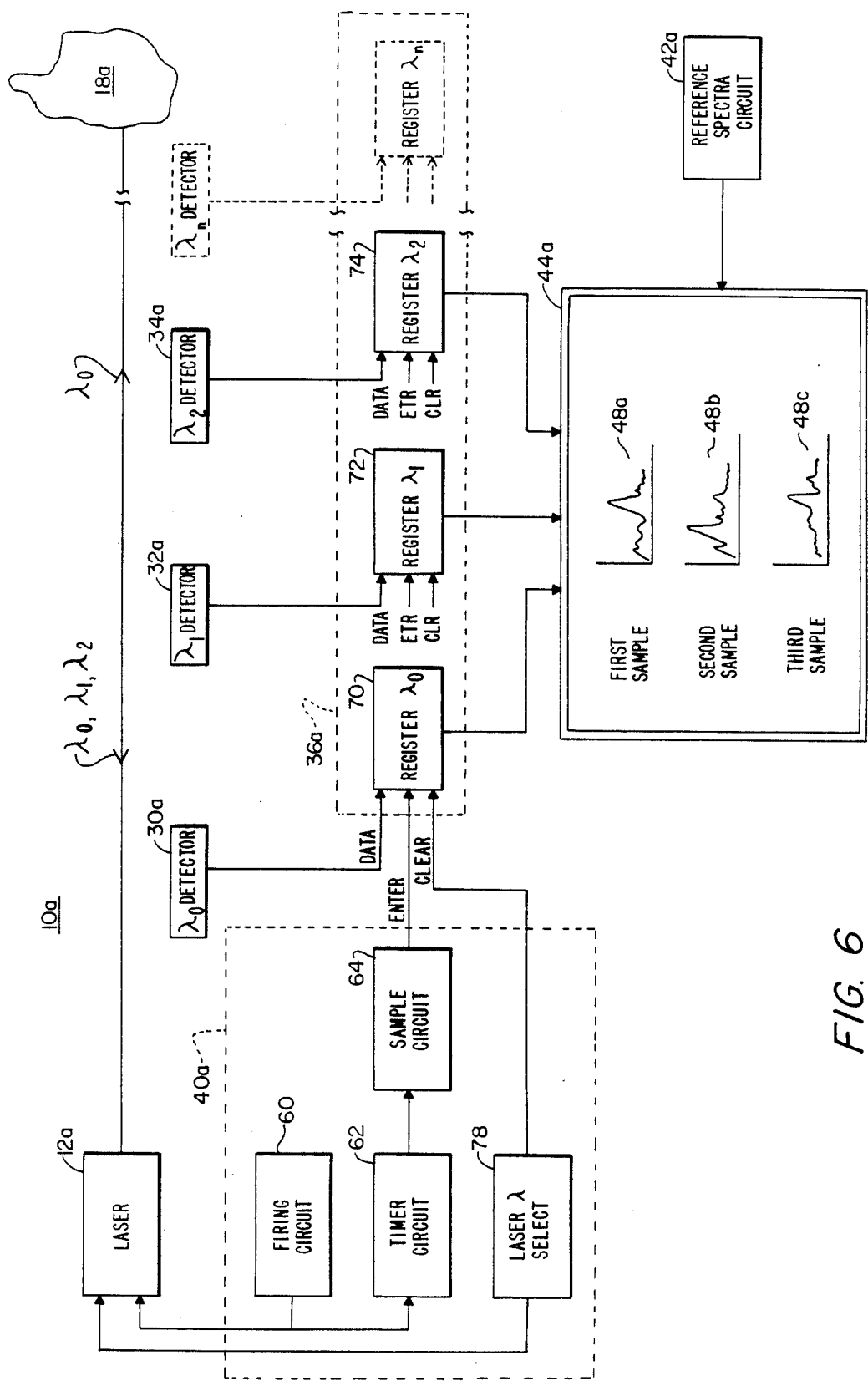
FIG. 6 is a more detailed schematic block diagram of a system according to this invention.

Control circuit 40a, FIG. 6, may include a firing circuit 60 which provides a trigger signal to pulse laser 12a and to simultaneously initiate operation of timer circuit 62, which after a period determined by the range of the unknown chemical species 18a operates sample circuit 64 to enter data from detectors 30a, 32a and 34a into registers 70, 72 and 74. Each time a sample is entered from the detectors to the registers, another spectrum such as spectrum 48 in FIG. 2, is provided. For example, after three sets of data have been entered in registers 70, 72 and 74, three spectra 48a, 48b and 48c may be provided to display 44a, which may be a monitor where the spectra 48a, 48b and 48c may be visually or automatically compared with known spectra received from reference spectra circuit 42aa. A number of samples may be made from each of the detectors and accumulated in the same stage of each register in order to integrate the outputs of the detectors over a period of time, thereby increasing the ratio of the signal to the background noise. Control circuit 40a may also include a laser wavelength select circuit 78, which can shift laser 12a output slightly to resolve ambiguities if identification cannot be positively made of the unknown chemical species. Laser select circuit 78 also provides a clear output to registers 70, 72 and 74, so that data from the new wavelength is not combined with data from other laser wavelengths.

Figure 7:
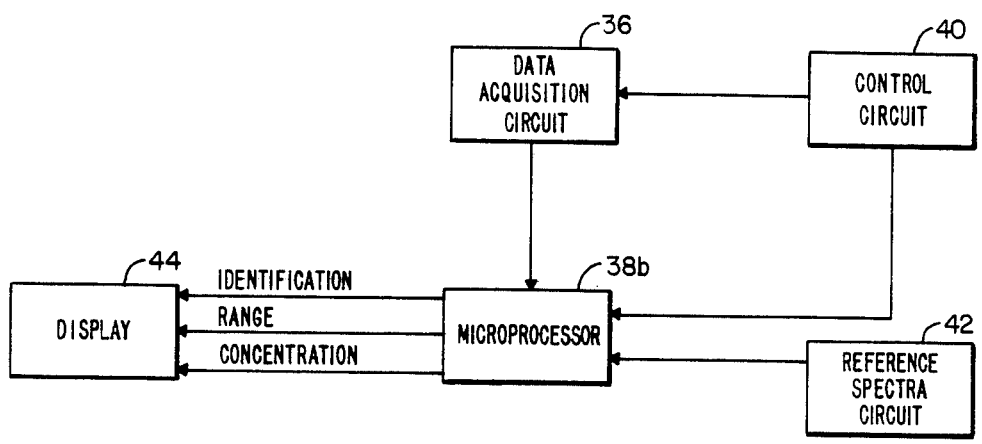
FIG. 7 is a block diagram of a portion of the system of this invention including a microprocessor for range and concentration determination.

The system may be expanded to incorporate more sophisticated information processing. The return radiation sensed by detectors 30a, 32a and 34a, FIG. 6, are utilized to determine the delay in the return of the radiation. This delay, the time between the firing of laser 12a and the appearance of a particular spectral feature, can be used to calculate the range to the mass of unknown chemical species. In one embodiment, comparator/analyzer circuit 38 includes a microprocessor 38b, FIG. 7, which determines the time interval between the laser firing and the return of an identified spectra, then divides that time by two and multiplies by the speed of light to determine the distance to the unknown mass. From the intensity of the signals from detectors 30, 32 and 34 and the range, a determination can be made of concentration of the unknown chemical species. This is accomplished in microprocessor 38b by multiplying the known concentration of the reference spectra by the square of the ratio of the range of the unknown chemical species to the range of the reference and the ratio of the intensity of the unknown chemical species to intensity of the reference spectra. If an ambiguity occurs, that is, if an unknown chemical species may be one of two possible species, then a new laser excitation wavelength may be used in the next excitation cycle.

Other embodiments will occur to those skilled in the art and are within the following claims:

What is claimed is:

1. A system for remote detection and identification of molecular species by laser initiated nonresonant infrared spectroscopy, comprising:
    an infrared pulsed laser source for providing radiation of a first wavelength;
    means for directing radiation at said first wavelength from said laser source to a remote mass of an unknown molecular species, which absorbs said radiation at said first wavelength to induce molecular excitation therein and emits nonresonant infrared radiation at one or more other wavelength regions, each said laser pulse having a duration less than the vibrational quenching time of said molecular species;
    means for receiving infrared radiation from said mass of unknown molecular species;
    means, responsive to said means for receiving, for detecting the intensity of the received infrared radiation;
    means for sampling the intensity of the received infrared radiation after molecular excitation during the period of enhanced emission before relaxation, to obtain a nonresonant emission spectrum characteristic of said unknown molecular species; and
    means for comparing said characteristic of said unknown molecular species with the characteristics of known molecular species for determining the identity of the unknown molecular species.

2. The remote detection and identification system of claim 1 in which said period of enhanced emission has a duration of $10^{-6}$ to $10^{-4}$ seconds.

3. The remote detection and identification system of claim 1 in which said means for sampling has sample intervals of 1 to 10 microseconds.

4. The remote detection and identification system of claim 1 in which said laser source provides radiation in the 8–14 $\mu$m range.

5. The remote detection and identification system of claim 1 in which said laser source includes a $CO_2$ laser.

6. The remote detection and identification system of claim 5 in which said laser source provides radiation in 9.4 $\mu$m region and said emissions are at 8–14 $\mu$m.

7. The remote detection and identification system of claim 1 in which said laser source provides radiation in 10.6 $\mu$m region and said emissions are at 8–14 $\mu$m.

8. The remote detection and identification system of claim 1 in which said unknown species is in the liquid phase.

9. The remote detection and identification system of claim 1 in which said unknown species is in the gaseous phase.

10. The remote detection and identification system of claim 1 in which said unknown species is an aerosol.

11. The remote detection and identification system of claim 1 further including ranging means, responsive to said means for receiving, for determining the time delay between the firing of the laser and the return of radiation including nonresonant radiation emitted from the mass of unknown molecular species in order to determine the range to the mass of unknown molecular species.

12. The remote detection and identification system of claim 11 further including means, responsive to the range of the unknown molecular species and the concentration and range of known species, for ascertaining the concentration of the unknown molecular species.

13. The system of claim 1 in which the duration of each laser pulse is less than ten microseconds.

14. The system of claim 1 in which said means for sampling has sample intervals less than the vibrational quenching time of said molecular species.

15. A method of remote detection and identification of molecular species by laser initiated nonresonant infrared spectroscopy comprising:
    providing infrared pulsed radiation of a first wavelength;
    directing radiation at said first wavelength to a remote mass of an unknown molecular species, which absorbs the radiation at said first wavelength to induce molecular excitation therein and emits nonresonant radiation in one or more other wavelength regions, each said laser pulse being directed at said unknown molecular species for a duration of less than the vibrational quenching time of said molecular species;
    receiving radiation from the mass of unknown molecular species;
    detecting the intensity of the received radiation;
    sampling the intensity of the received radiation after molecular excitation during the period of enhanced emission before relaxation, to obtain a nonresonant emission spectrum characteristic of the unknown molecular species; and
    comparing said characteristic of said unknown molecular species with the characteristics of known molecular species for determining the identity of the unknown molecular species.

16. The method of remote detection and identification of claim 15 further including detecting the time delay between the firing of the laser and the return of radiation including nonresonant radiation emitted from the mass of unknown molecular species in order to determine the range to the mass of unknown molecular species.

17. The method of remote detection and identification of claim 16 further including ascertaining the concentration of the unknown molecular species from the range of the unknown molecular species and the range and concentration of the known species.

* * * * *